US00PP20774P2

(12) United States Plant Patent
Skaggs

(10) Patent No.: US PP20,774 P2
(45) Date of Patent: Feb. 23, 2010

(54) ***HOSTA* PLANT NAMED 'EMPRESS WU'**

(50) Latin Name: *Hosta hybrida*
Varietal Denomination: Empress Wu

(76) Inventor: Brian Skaggs, 13620 W. 173 Ave., Lowell, IN (US) 46356-9495

( * ) Notice: Subject to any disclaimer, the term of this patent is extended or adjusted under 35 U.S.C. 154(b) by 0 days.

(21) Appl. No.: 12/313,138

(22) Filed: Nov. 17, 2008

(51) Int. Cl.
*A01H 5/00* (2006.01)

(52) U.S. Cl. ..... Plt./353

(58) Field of Classification Search ..... Plt./353
See application file for complete search history.

*Primary Examiner*—Kent L Bell

(57) ABSTRACT

*Hosta* plant named 'Empress Wu' is a new cultivar with very large green leaves, gigantic plant stature in the landscape, light lavender flowers and large matching bracts producing a water lily effect, suitable as a potted plant, for the garden, and for cut flower arrangements.

2 Drawing Sheets

Botanical classification: *Hosta hybrida* (Tratt.)
Variety denomination: 'Empress Wu'

BACKGROUND OF THE INVENTION

The present invention relates to the new and distinct *hosta* plant, *Hosta* 'Empress Wu' hybridized and developed by Brian Skaggs and Virginia Skaggs in Lowell, Ind., USA as the result of a selfing of *Hosta* 'Big John' (not patented). The plant has been successfully asexually propagated by division in Lowell, Ind. and also by tissue culture at a nursery in Zeeland, Mich. and in both systems found to be stable and produce identical plants that maintain the unique characteristics of the original plant.

BRIEF SUMMARY OF THE INVENTION

*Hosta* 'Empress Wu' differs from its parent, 'Big John', as well as all other *hostas* known to the applicant. The most similar known *hosta* cultivars: 'T Rex' (not patented), 'Elatior' (not patented), 'Vim and Vigor' (not patented) and *Hosta montana macrophylla* (not patented) are all green cultivars with large foliage and landscape stature. The new plant is larger than all of these in both leaf and plant habit. 'T Rex' has a more rounded leaves with deeper veining, more corrugation while the flowers are much lighter in color (near white), and the plant is slower growing. 'Elatior' has a much lighter green leaf, lighter colored flowers and longer arching scapes. 'Vim and Vigor' has a smaller leaf and habit, medium lavender flowers and the scape is longer and arching. The species *Hosta montana macrophylla* generally has a smaller cascading leaf with a more acutely pointed apex and is much slower growing.

There are over 3,800 cultivars registered with The American Hosta Society, which is the International Cultivar Registration Authority for the genus *Hosta*. *Hosta* 'Empress Wu' differs from these and all unregistered cultivars known to the inventor in the following combined traits:

1. Huge foliage starting off with slight glaucous surface and becoming dull to slightly shiny.
2. Extremely large landscape stature.
3. Tightly compact light lavender flowers on short scapes just above foliage.

4. Each flower and bud is subtended by a large bract of a matching light lavender color producing a water-lily flower appearance while still in bud.

BRIEF DESCRIPTION OF THE DRAWINGS

The photographs of the new plant demonstrate the overall appearance of the mature plant, including the unique traits, grown in a partially shaded garden in Lowell, Ind. The colors are as accurate as reasonably possible with color reproductions. Ambient light spectrum, source, direction and temperature may cause the appearance of minor variation in color.

DETAILED BOTANICAL DESCRIPTION

Figure 1:
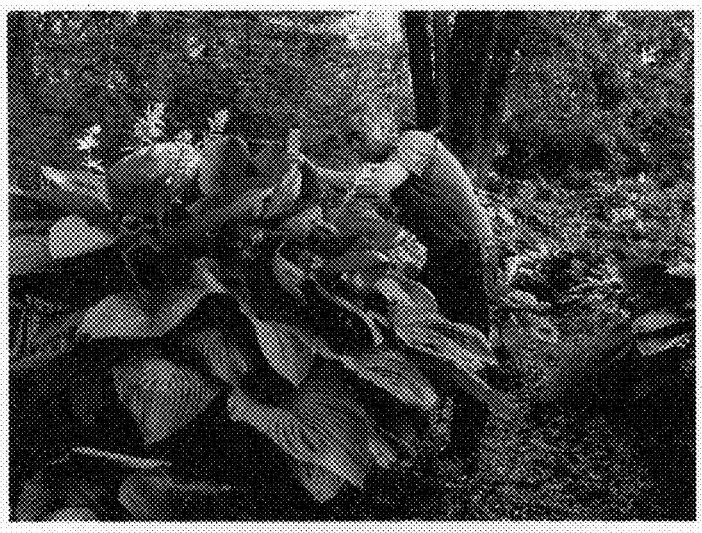
FIG. 1 shows the new plant in a landscape setting.
Figure 2:
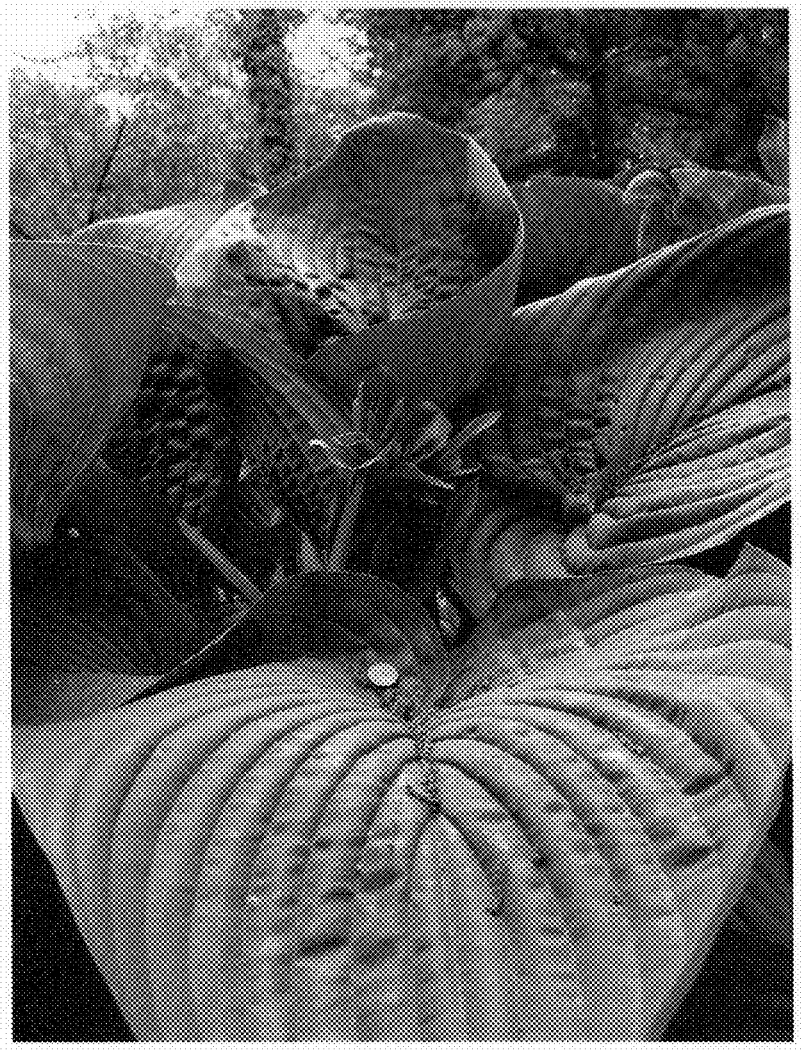
FIG. 2 shows a close-up of the foliage.
Figure 3:
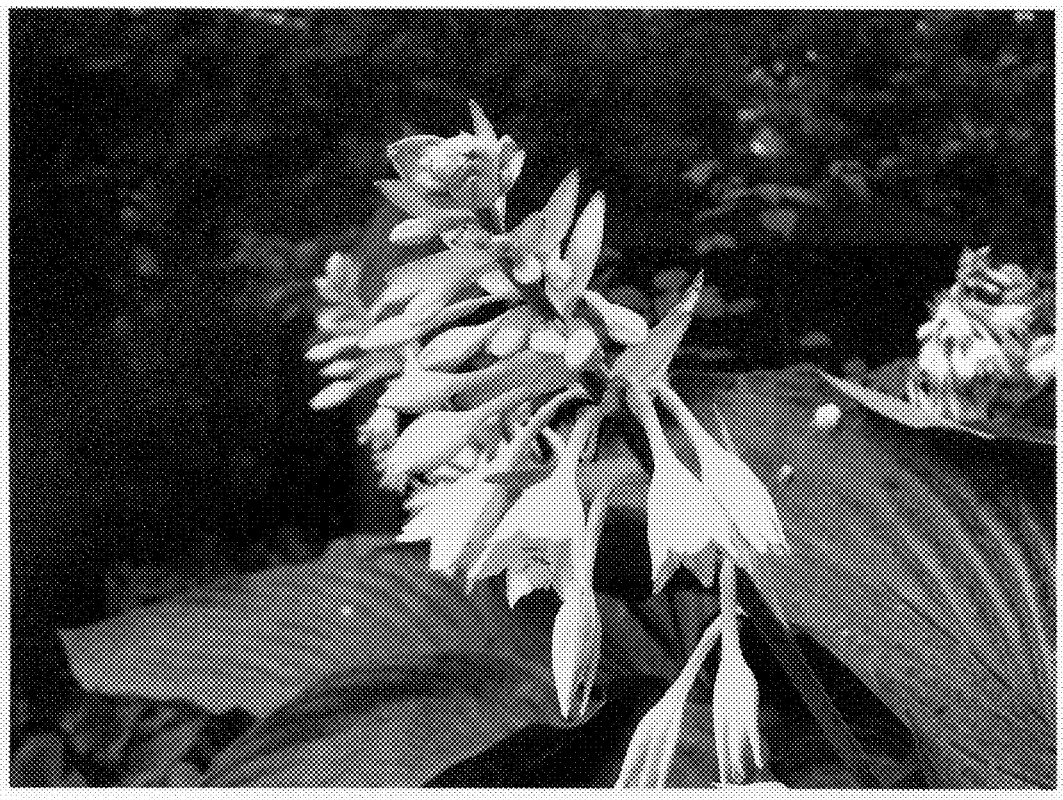
FIG. 3 shows the foliage flower scape.
Figure 4:
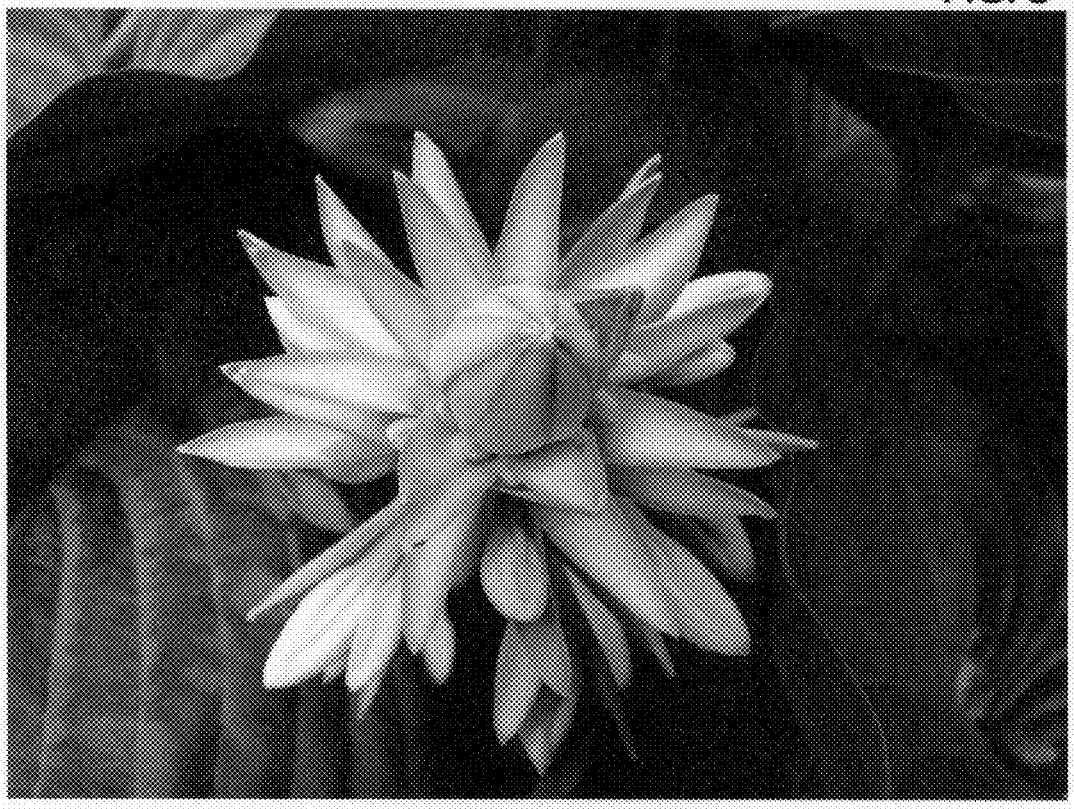
FIG. 4 shows the flower scape at bud stage with the water-lily flower effect.

The following descriptions and color references are based on the 2001 edition of The Royal Horticultural Society Colour Chart except where common dictionary terms are used. The new plant, *Hosta* 'Empress Wu', has not been observed under all possible environments. The phenotype may vary slightly with different environmental conditions, such as temperature, light, fertility, moisture and specimen maturity, but without any change in the genotype. The following observations and size descriptions are of a six-year old plant in a garden in Lowell, Ind. in a lightly shaded landscape with supplemental water and light fertilizer.

Botanical classification: *Hosta* hybrid;

Parentage: *Hosta* 'Big John' (not patented) times 'Big John';

Propagation method: by sterile laboratory tissue culture division and garden division;

Growth rate: rapid;

Crop time: summer growing 8 to 9 weeks to finish in a one-liter container;

Time to initiate roots from tissue culture about two weeks;

Plant description:

*Plant shape and habit.*—Hardy, herbaceous, upright as juvenile and mounded in maturity, forming perennial with basal rosette leaves, usually bilateral and radially symmetrical, spreading by rhizomes;

*Roots.*—Normal, fleshy, lightly branching, cream-colored in normal soil;

*Plant size.*—Foliage height of a mature plant at flowering that was six-year old is about 120 cm tall; tallest measured foliage is about 128 cm; width of plant at the widest point is approximately 275 cm at the widest point;

Foliage description:

*Leaf blade.*—Cordate leaf base with acute apex, mostly bilaterally symmetrical, entire margins, mostly flat blades with impressed veins; width to length ratio of about 1:1.1; largest leaves about 71 cm long and 64.5 cm wide; average about 56 cm long and 51 cm wide; 17 to 18 pairs of major parallel veins; top surface begins season slightly glaucous becoming dull matte surfaced to slightly shiny, and bottom surface is glaucous and tends to stay through most of the season;

*Blade color.*—Adaxial (top) darker than RHS 137A; abaxial (underside) nearest RHS 191A with a glaucous bloom;

*Veins.*—17 to 18 pairs of major parallel veins, deeply impressed; same color as surrounding top and bottom leaf surfaces;

*Petioles.*—Variable with the petioles of center shoots larger, 75 to 84 cm long, about 3.8 cm wide measured at 7 cm above soil line;

*Petiole color.*—Outside of petiole nearest RHS 139D with a slight glaucous surface; inside of petiole lighter than RHS 138D;

Flower description:

*Buds.*—Clavate with bluntly acute apex and longer thin base; one day prior to opening nearest RHS 91D near base and RHS 92D at middle and apex; about 5.5 cm long, and 2.0 cm wide at the broadest portion;

*Flowers.*—30 to 40 per scape; tightly arranged with about 6 to 8 flowers per 1.0 cm centimeter of scape in some areas and spaced 1 cm apart in other areas; funnelform; about 4.0 cm wide and 7.0 cm long, (distal flowers opening smaller); remain open for a normal period, usually one to two days on or cut from plant; scapes remain effective from early June into mid July in Lowell, Ind.; no detectable fragrance;

*Tepal.*—Two identical sets of three fused at the basal two thirds; acute apex; margins entire; approximately 7.0 cm long and 2.0 cm wide; tepal color nearest RHS 91D on outside and RHS 76C on the inside; veins on the inside nearest RHS 76C and on outside nearest RHS 91D;

*Pedicel.*—Approximately 26 mm long, 2 mm wide, between RHS 138C and RHS 138 B with violet undertones;

*Peduncle.*—Usually one per division, erect to slightly arching, about 8 mm diameter at base, average 130 cm tall, some bending and staying partially below foliage; RHS N138B;

*Gynoecium.*—Single; Style: about 7.0 cm long, 1 mm diameter, curled upward at distal 1.0 cm; lighter than RHS 155D; Stigma: 1 mm to 2 mm in diameter, lighter than RHS 155D;

*Androecium.*—Filaments: six, about 1.0 mm in diameter and 7.5 cm long, curving upward the last 1.5 cm; lighter than RHS 155D;

*Anthers.*—oblong; dehiscing along the center longitudinal axis; about 6.0 mm long and 2.0 mm wide, closest to RHS N77A;

*Pollen.*—elliptical, less than 0.1 mm long, nearest RHS 13B;

*Bracts.*—subtending one or more flowers, sessile, lanceolate, widest at base and tapering to acute apex; protruding upward about 80 degree angle away from scape; lowest up to 8.5 cm long and 1.5 cm wide before first flower, progressively decreasing in both length and width;

*Bract color.*—lowest bracts nearest RHS 138B on top and bottom surfaces in the terminal half and lighter than RHS 138D on the basal top portion and nearest RHS 138C on the basal outer portion; the more distal bracts quickly becoming more lavender tinted to becoming between RHS 91C and RHS 91B;

*Fruit.*—tri-dehiscent capsule, about 4 cm long and 7 mm wide; variable in color at dehiscence including: RHS 164B with more green or more yellow;

*Seeds.*—single winged drupe, about 12 mm long and 3 mm wide; about 30 per pod; black nearest RHS 202A;

*Disease resistance.*—Slug feeding on mature plants has not been noticed. Other disease or pest resistance beyond that common to *hostas* has not been observed. The plant grows best with light fertilizer, plenty of moisture and adequate drainage, but is able to tolerate some flooding and drought when mature. Hardiness at least from USDA zone 3 through 9, and other disease resistance is typical of that of other *hostas*.

I claim:

1. A new and distinct ornamental *Hosta* plant named 'Empress Wu' as herein described and illustrated, with very large green leaves and plant stature, light lavender flowers and large matching bracts producing a water lily effect, suitable as a potted plant, for the garden, and for cut flower arrangements.

* * * * *